United States Patent [19]

Walters

[11] 4,060,708
[45] Nov. 29, 1977

[54] METASTABLE ARGON STABILIZED ARC DEVICES FOR SPECTROSCOPIC ANALYSIS

[75] Inventor: John P. Walters, Madison, Wis.

[73] Assignee: Wisconsin Alumni Research Foundation, Madison, Wis.

[21] Appl. No.: 614,194

[22] Filed: Sept. 17, 1975

[51] Int. Cl.² .............................................. B23K 9/00
[52] U.S. Cl. .................................. 219/121 P; 219/75;
  250/425; 313/201; 313/231.3; 315/111; 356/85
[58] Field of Search .................... 219/74, 75, 121 P;
  250/425; 313/201, 203, 231.3; 315/111; 356/85

[56] References Cited

U.S. PATENT DOCUMENTS

| | | | |
|---|---|---|---|
| 3,042,830 | 7/1962 | Orbach | 219/75 X |
| 3,149,222 | 9/1964 | Giannini et al. | 219/121 P |
| 3,217,162 | 11/1965 | Wehner | 356/85 X |
| 3,304,460 | 2/1967 | Cargill, Jr. et al. | 219/121 P X |
| 3,424,533 | 1/1969 | Hughes et al. | 356/85 |
| 3,467,471 | 9/1969 | Geenfield et al. | 356/85 X |
| 3,533,756 | 10/1970 | Houseman | 219/121 P X |
| 3,601,578 | 8/1971 | Gebel et al. | 219/121 P |
| 3,712,996 | 1/1973 | Kugler | 219/121 P X |

Primary Examiner—J. V. Truhe
Assistant Examiner—N. D. Herkamp
Attorney, Agent, or Firm—Burmeister, York, Palmatier, Hamby & Jones

[57] ABSTRACT

A device is disclosed for producing an electrical arc which is stabilized by a stream of metastable argon, or some other stabilizing gas. The arc may be employed to vaporize a sample material so as to produce light for spectroscopic analysis. The vaporization is rapid so that the constituents of the sample material can be determined very quickly and accurately. The arc is highly stable so that it operates without sputtering, dancing or showing other signs of instability. Thus, the results obtained with the arc are highly accurate and repeatable. The arc is produced between a cathode in one end of an arc chamber and an anode outside the opposite end of the chamber. The arc passes out of the chamber through an orifice in a gas shaping nozzle. Argon gas is supplied to the chamber through a plurality of gas inlets, which preferably are directed at angles having peripheral components so that a whirling motion is imparted to the gas as it enters the chamber. The gas is discharged steadily out of the chamber through the nozzle and toward the anode in a restricted, shaped and controlled amount, so that the gas plays in a sloped beam over the anode. The sample material to be analyzed is preferably contained within a cavity in the anode, which is heated to a high temperature by the arc, so that the sample material will be vaporized.

23 Claims, 5 Drawing Figures

U.S. Patent    Nov. 29, 1977    4,060,708
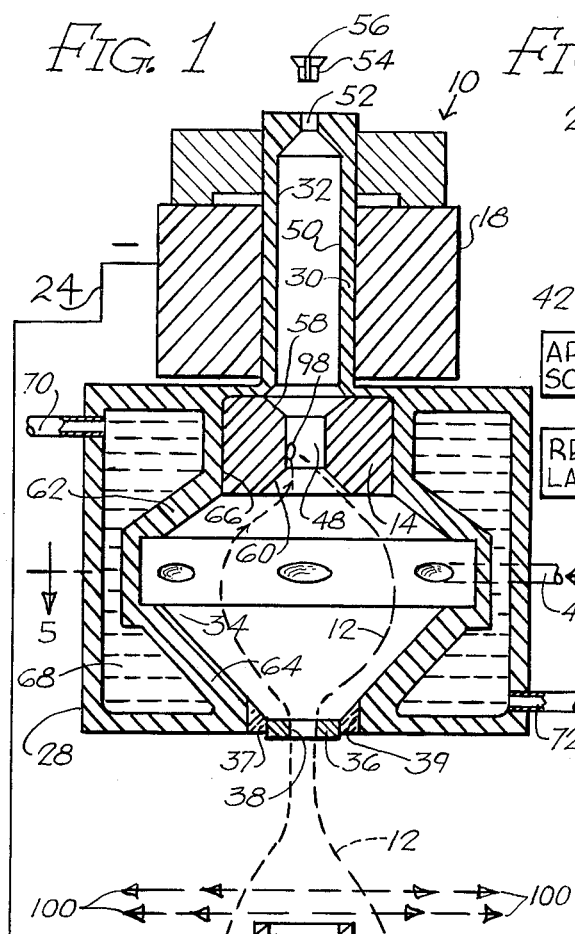
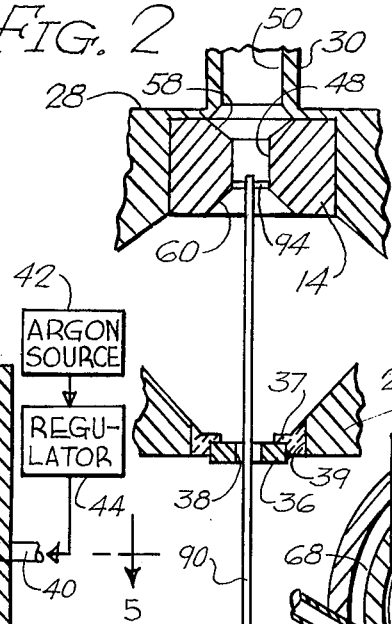
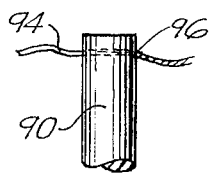
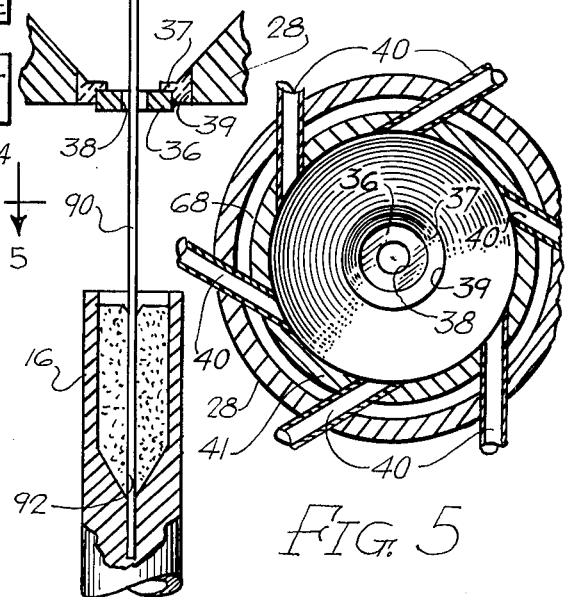
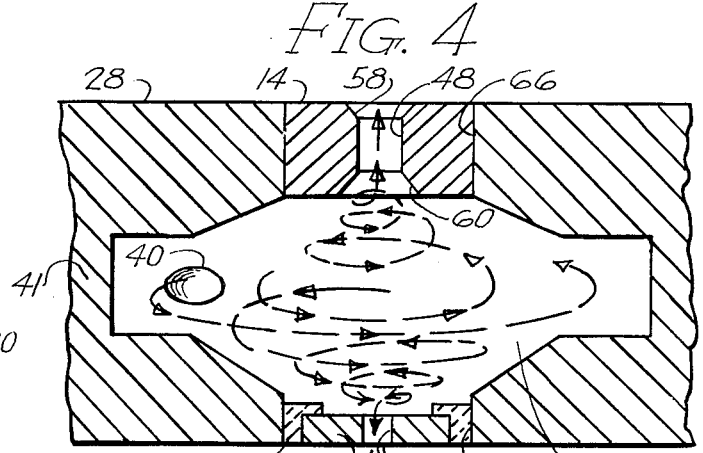
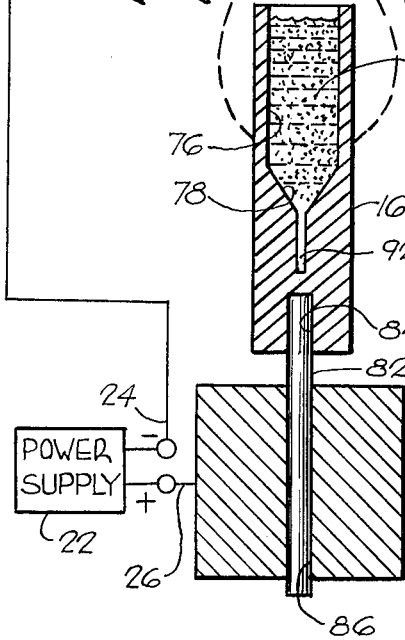

METASTABLE ARGON STABILIZED ARC DEVICES FOR SPECTROSCOPIC ANALYSIS

This invention relates to a device for producing a stabilized electric arc which may be employed to vaporize sample materials for spectroscopic analysis. The vaporization of the sample material produces spectral lines and other formations which can be analyzed to determine the constituents of the sample material very accurately and quickly. Because of the stability of the arc, the results obtained by spectroscopic analysis are highly reliable and repeatable.

One object of the present invention is to provide a new and improved device for producing an electrical arc which is stabilized by a steady flow of metastable argon, or some other stabilizing gas.

This object is accomplished by providing a housing having an arc chamber therein from which a stream of argon or some other stabilizing gas is discharged through an orifice in a gas shaping nozzle. An electrical arc is produced between a cathode inside the chamber and an anode outside the chamber, opposite the nozzle. The arc is guided and stabilized by the stream of argon, which plays over and partially envelops the anode. The argon is converted to its metastable state by the arc within the housing. The metastable state may be associated with the neutral atom (Ar°) or the first ion (Ar+). Some mixing of the two species may also occur. The presence of the neutral metastable, which is itself easily ionized, or the ionic metastable, which is long lived (even at the atmospheric pressure) enhances the stabilizing action of the argon stream as it conducts the full arc current between the cathode electrode inside the arc chamber and the anode electrode outside the arc chamber. Preferably, the sample material is in the solid state. This may be a finely powdered solid, a collection of shavings or drillings of a metal, a blend of powders, such as graphite and other powders, or a liquid sample evaporated onto a carrier powder. Solids other than powders may be used, restrictive to their macroscopic behavior and melting characteristics under the influence of the arc current and subsequent heating. The sample material may also be blended with other substances with which it will react at high temperatures, such as cationic halides or oxides or carbides, and form eutectics or the like to promote or inhibit the formation of a particular atomic or molecular vapor under the thermal heating caused by the arc. In such cases it may be desirable to shape the anode electrode in one or more of the forms associated with a high temperature furnace.

The flow of arc gas across, around and over the anode electrode causes it to be intensely heated so that sample material in and on the electrode is vaporized. The vaporized sample material will usually emit light, which can be analyzed spectroscopically, but also may be present in the vapor state in an unexcited form such that it will absorb light. Thus the selective line or molecular band absorption may be monitored spectroscopically for purposes of chemical analysis of the sample. In the process of absorbing light from another (primary) light source, the vaporized sample may become excited to fluoresce, and the fluorescent emission analyzed spectroscopically for purposes of chemical analysis of the sample. It is to be understood that only because of the highly controlled and stable vaporization of the sample from the anode, due to the action of the metastable argon stream playing over the anode, these methods of spectroscopic analysis are possible in a straight-forward, reproducible, and accurate manner.

The cathode and the nozzle are preferably along the axis of the arc chamber, which is preferably symmetrical about such axis. The argon is supplied to the chamber through a plurality of inlets which are disposed symmetrically around the axis and are directed at angles having tangential or peripheral components so that a whirling motion is imparted to the argon within the chamber.

The gas shaping nozzle in the housing is preferably in the form of a floating electrode which is electrically insulated from the cathode. In addition to such nozzle in the housing, the cathode may be formed with an opening leading to a cathode ballast chamber having a small relief port. This construction improves the stability of the arc.

To facilitate the striking of the arc, a slender elongated striker rod may be mounted on the anode. A socket to receive the striker rod may be formed in the bottom of the cavity in the anode. The striker rod is used by inserting it through the orifice in the neutral electrode and into the arc chamber. Preferably, an electrically conductive thread is mounted on the end of the striker rod, so that the thread will engage the cathode when the end of the striker rod is inserted into the ballast opening in the cathode. The striker rod and the thread are preferably made of graphite. The extreme heat produced by the arc current quickly vaporizes the thread and the striker rod, so that the arc is established between the cathode and the anode. Other means for striking the arc may be employed.

Further objects, advantages and features of the present invention will appear from the following description, taken with the accompanying drawings, in which:

FIG. 1 is a diagrammatic elevational section showing a stabilized arc device to be described as an illustrative embodiment of the present invention.

FIG. 2 is a fragmentary elevational section, similar to FIG. 1, but showing the use of the striker rod to strike the arc.

FIG. 3 is a fragmentary enlarged elevation showing the end of the striker rod and the electrically conductive thread thereon.

FIG. 4 is a fragmentary elevational section showing the movement of the argon as it whirls in the arc chamber and is discharged through the axial gas shaping nozzle.

FIG. 5 is a fragmentary cross-section, taken generally along the line 5—5 in FIG. 1.

As just indicated, the drawings illustrate a device or apparatus 10 for producing an electrical arc 12 between first and second electrodes 14 and 16. In accordance with the present invention, the electrode 14 preferably constitutes the cathode, while the electrode 16 constitutes the anode.

The electrodes 14 and 16 are adapted to be supported by a pair of jaws 18 and 20 which are movable toward and away from each other. Such movement makes it possible to strike the arc and to regulate the length of the arc.

The electrical current to produce the arc is provided by a suitable power supply 22 having its direct current output connected to the jaws 18 and 20. As shown, the negative output terminal of the power supply 22 is connected to the upper jaw 18 by an electrical lead 24, while the positive terminal is connected to the lower jaw 20 by an electrical lead 26.

The illustrated cathode 14 is mounted within a cathode housing 28 which may be made of stainless steel or some other suitable material, which preferably is electrically conductive. The illustrated housing 28 has a cylindrical stem or projection 30 which is securely mounted within a circular opening 32 in the upper jaw 18.

An arc chamber 34 is formed within the cathode housing 28 and is illustrated as being generally circular in horizontal cross-section. It will be seen that the cathode 14 is mounted in the housing 28 at one end of the chamber 34. In this case, the cathode 14 is in the form of a ring or disc and is mounted at the upper end of the chamber 34, which has a vertical axis. The cathode 14 may be made of graphite or some other material which is highly resistant to heat and to the erosion produced by the electrical arc.

A gas shaping nozzle 36 is preferably mounted in the housing 28 at the opposite end of the arc chamber 34. Thus, the nozzle 36 is at the lower end of the housing 34 in this instance. The nozzle 36 is formed with an orifice 38 which constricts and shapes the arc 12 as it passes between the cathode 14 and the anode 16. The nozzle 36 may be made of graphite of some other material which is highly resistant to heat. The nozzle 36 is preferably made of an electrically conductive material, but is insulated from the housing 28, as by means of the illustrated insulating ring 37, so that the nozzle may function as an intermediate electrode. In this case, the nozzle 36 is securely fitted into an opening 39 in the housing 28. The insulating ring 37 is made of an insulating, heat-resistant material, such as boron nitride or a suitable ceramic material, for example.

The nozzle or intermediate electrode 36 is preferably allowed to float electrically, so that it will assume the electrical potential of the portion of the arc 12 which is passing through the orifice 38 in the nozzle 36. With this mode of operation, the potential of the nozzle or electrode 36 is indeterminate. The potential of the nozzle or electrode 36 will depend upon the conditions under which the arc 12 is operating. As will be discussed in greater detail presently, the voltage assumed by the nozzle 36 may be measured by using a suitable voltmeter. The measured voltage provides an indication as to the operating conditions of the arc. If desired, the nozzle 36 may be supplied with a definite operating voltage from the power supply 22, or from a separate power supply. The voltage supplied to the nozzle 36 is generally an intermediate voltage, less than the full voltage between the cathode 14 and anode 16. The voltage supplied to the nozzle 36 has an influence upon the operation of the arc 12.

A stabilizing gas, preferably argon, is introduced into the arc chamber 34, so that a steady stream of the gas will be discharged through the orifice 38 in the nozzle 36. It is desirable to maintain laminar flow in the argon stream. The anode 16 is opposite the orifice 38 in the nozzle 36, so that the stream of gas is directed toward the anode 16. The argon plays over the anode 16 and partially envelops it. The electrical arc 12 follows the stream of gas, which directs and stabilizes the arc so that it operates in a quiet and steady manner, without sputtering, dancing or other signs of instability. The rate of flow of the argon gas is determined by the size of the orifice 38 in the nozzle 36, and the pressure of the gas in the arc chamber 34. Within the chamber 34, the arc 12 converts the argon to its metastable state, with the result that the stability of the arc is enhanced.

When the nozzle 36 is allowed to float electrically, the potential assumed by the nozzle is influenced by the flow of the argon through the nozzle 36 to the anode 16. If desired, the electrical potential of the nozzle 36 may be measured with a suitable voltmeter, in order to assist in optimizing the flow of the argon through the nozzle 36 to the anode 16.

It is also possible to employ a variable power supply to supply an adjustable voltage to the nozzle 36, to aid in shaping the argon beam as it passes through the nozzle.

It is preferred to supply the argon gas to the chamber 34 through a plurality of inlets or conduits 40, extending into the arc chamber 34 through an annular side wall 41, which is preferably circular in cross-section. The inlet conduits 40 are preferably spaced at equal intervals around the annular side wall 41 and are directed at angles having tangential or peripheral components, so that the argon gas will be given a whirling motion within the chamber 34. The argon may be supplied to the inlet conduits 40 from an argon tank or some other source 42, through a regulator 44 which controls the amount of argon supplied to the chamber 34. The regulator 44 may be adjusted to vary the rate of flow of the argon.

The provision of a plurality of the inlet conduits 40 insures that the argon will be supplied uniformly to all portions of the chamber 34 so that the argon will be discharged with a high degree of stability through the orifice 38. The angling of the inlet conduits 40, to produce whirling movement of the argon, also improves the steadiness with which the argon is discharged through the orifice 38 in the nozzle 36.

It is preferred to provide for the discharge of some of the argon through the cathode 14. For this purpose, the cathode 14 is formed with an axial ballast opening 48. The lower end of the opening 48 communicates with the arc chamber 34, while the upper end communicates with a cathode ballast chamber 50 within the stem portion 30, which is generally tubular in shape. At the upper end of the stem portion 30, the ballast chamber 50 narrows down to form a smaller aperture 52. For the purpose of restricting the discharge of the argon, it is preferred to mount a cathode ballast chamber relief plug or bushing 54 within the aperture 52. The plug 54 has a small axial aperture 56 which greatly restricts and meters the flow of the argon, so that only a small amount is allowed to leak out through the cathode ballast opening 48 in the electrode 14.

As illustrated, the cathode ballast opening 48 in the cathode 14 is generally cylindrical in shape but has flaring upper and lower portions 58 and 60 which are frusto-conical in shape.

The annular side wall 41 of the arc chamber 34 is generally cylindrical in shape. The cylindrical side wall 41 connects with upper and lower frusto-conical walls 62 and 64 which form the end walls of the arc chamber 34. The opening 39 for the insulating ring 37 is formed in the central portion of the lower frusto-conical wall 64. The cathode 14 is securely fitted into an opening 66 formed in the central portion of the upper frusto-conical wall 62.

Provision is made for causing water or some other cooling medium to flow through the housing 28, around the walls 41, 62 and 64 of the arc chamber 34, so as to remove much of the heat generated by the electrical arc. Thus, the housing 28 is formed with a hollow annular space or passage 68, disposed around the walls 41, 62 and 64. Inlet and outlet pipes or conduits 70 and 72 are connected to the annular space 68 so that water or some other cooling medium can be circulated through the space 68.

The external anode 16 is preferably provided with means for holding a supply of the sample material to be analyzed. In this case, the electrode 16 is in the form of a generally cylindrical rod, formed with a cavity or crater, which is illustrated as a generally cylindrical bore 76 having a conically tapered lower end portion or bottom 78. The cavity 76 acts as a receptacle to hold a quantity of the material 80 to be analyzed. The anode 16 is preferably made of graphite or some other electrically conductive material which is highly resistant to heat.

As previously indicated, the sample material is preferably in the form of a solid which may be powdered or otherwise finely divided. However, the sample material to be analyzed may also be in the form of a liquid, which may be evaporated onto a solid substrate made of a material having the desired thermal properties under the influence of the arc.

The anode is suitably supported on the lower jaw 20. As shown, the anode 16 is supported by a post 82 which is securely received in a socket 84, formed in the lower end of the anode 16. The post 82 is securely received in an opening 86 formed in the jaw 20.

As previously indicated, the arc may be started in various ways. As shown in FIG. 2, it is preferred to employ an electrically conductive striker rod 90 to assist in striking the arc 12 between the electrodes 14 and 16. The illustrated striker rod 90 is slender and elongated, and preferably is circular in cross-section. The striker rod 90 is preferably made of graphite or some other electrically conductive material.

The striker rod 90 is similar to the fine graphite rods used for mechanical pencils. In fact, the same kind of graphite rod stock used for mechanical pencils can be used for the striker rod 90.

It will be seen from FIG. 2 that the striker rod 90 is mounted on the anode 16 and is adapted to be inserted upwardly through the orifice 38 in the nozzle 36. The illustrated anode 16 is formed with a socket or opening 92 for receiving and supporting the striker rod 90. The socket 92 may be centrally located in the bottom of the cavity 76 in the anode 16.

The striker rod 90 is smaller in diameter than the orifice 38 in the nozzle 36, so that the rod 90 can easily be inserted through the orifice and brought into electrical contact with the cathode 14. To facilitate the establishment of such contact, it is preferred to mount an electrically conductive thread 94 on the upper end portion of the striker rod 90. The thread 94 is preferably made of graphite. As shown to best advantage in FIG. 3, the graphite thread 94 may be inserted through a transverse hole or opening 96, formed through the upper end portion of the striker rod 90. Other means may be employed for mounting the thread 94 on the rod 90. For example, the thread 94 may be inserted into a narrow slot formed across the upper end of the striker rod 90.

The upper end portion of the striker rod 90 may be inserted into the cathode ballast opening 48 in the ring-shaped cathode 14. As the rod 90 is inserted into the opening 48, the graphite thread 94 comes into electrical contact with the cathode 14.

Prior to the insertion of the striker rod 90, the power supply 22 is preferably energized, so that a voltage is produced between the cathode and anode 14 and 16. When the graphite thread 94 engages the cathode 14, a current flows along the striker rod 90 and the thread 94 between the anode 16 and the cathode 14. The current may be quite large, so that considerable heat is generated in the thread 94 and the striker rod 90, due to the electrical resistance of these components. The heat rapidly vaporizes the graphite thread, so that an electrical arc is struck between the cathode 14 and the striker rod 90. The heat of the arc and the resistance heating due to the flow of the arc current along the striker rod 90 quickly vaporizes the striker rod, so that the electrical arc is struck between the cathode 14 and the anode 16. The arc passes through the orifice 38 in the nozzle 36. The arc forms a cathode spot 98 inside the ballast opening 48 in the cathode ring 14, as will be discussed in greater detail presently.

It is generally preferred to start the flow of the argon gas from the source 42 before the arc is struck. The flow of the argon is closely controlled by the regulator 44. The argon enters the arc chamber 34 through the inlets 40, which are directed at angles having peripheral components, so that a whirling motion is imparted to the gas within the chamber 34, as shown in FIG. 4. The argon gas fills the arc chamber 34 and is projected outwardly through the orifice 38 in the nozzle 36. The argon travels from the orifice 38 to the anode 16 and at least partially engulfs the anode.

Between the nozzle 36 and the anode 16, the arc 12 follows the stream of argon and is stabilized and directed by the argon.

Within the chamber 34, the argon is raised to its metastable state by the electrical arc. The metastable state of the argon, as it is discharged from the arc chamber 34 through the orifice 38 in the nozzle 36, is an important factor in effectively stabilizing the arc.

A small amount of the argon gas leaks upwardly through the cathode ballast opening 48 in the cathode 14 and escapes through the small aperture 56 in the relief plug 54. This argon leak through the cathode 14 ensures that all of the air in the chamber 34 will be replaced with argon, and that the arc will be struck in an argon atmosphere. The stability of the arc is improved by insuring that the entire arc chamber 34 is filled uniformly with the argon gas.

The formation and maintenance of the cathode spot 98 on the inside of the cathode ring 14 is believed to be a unique and highly advantageous feature of the present invention, contributing greatly to the stability of the arc 12. In a conventional arc discharge, the cathode spot is observed to wander rapidly over a large area of the cathode electrode. The arc column in a conventional arc discharge is observed to follow this wandering of the cathode spot, so that instability is a problem in the conventional arc discharge. In the arc device of the present invention, this problem of instability has been overcome by forming the cathode 14 in the form of a ring, and by causing the cathode spot 98 to be established and maintained within the cathode ring 14. When the arc 12 is struck, the cathode spot 98 is established on the inside of the cathode ring, as previously described. The arc is held inside the cathode ring 14 by the small upward flow of argon through the cathode ballast opening 48 in the cathode ring 14. This flow is metered by the small aperture 56 in the relief plug 54. During the normal operation of the arc 12, the wandering of the cathode spot 98 is confined within the small opening 48 in the cathode ring 14. This slight wandering has only a negligible effect upon the arc 12. Thus, as the arc emerges from the orifice 38 in the nozzle 36, the arc is controlled by the argon flow pattern, and not by the slight wandering of the cathode spot 98.

A wide variety of sample materials may be employed. Preferably, the sample material is in the solid state. The sample material may be a finely powdered solid, a collection of shavings or drillings of a metal, a blend of powders, such as graphite and other powders, or a liquid sample evaporated onto a carrier powder. Solids other than powders may be used, restrictive to their macroscopic behavior and melting characteristics under the influence of the arc current and subsequent heating. The sample material may also be blended with other substances with which it will react at high temperatures, such as cationic halides or oxides or carbides, and form eutectics or the like to promote or inhibit the formation of a particular atomic or molecular vapor under the thermal heating caused by the arc. In such cases it may be desirable to shape the anode electrode in one or more of the forms associated with a high temperature furnace.

For example, a solid sample material may be reduced to a fine powder and mixed with powdered graphite and a fractional distillation material, such as sodium fluoride. The mixture may then be placed in the cavity 76 of the anode 16 and may be tamped firmly in place.

The flow of the arc gas across, around and over the anode electrode 16 causes it to be intensely heated so that sample material in and on the electrode is vaporized. The vaporized sample material will usually emit light, which can be analyzed spectroscopically, but also may be present in the vapor state in an unexcited form such that it will absorb light. Thus the selective line or molecular band absorption may be monitored spectroscopically for purposes of chemical analysis of the sample. In the process of absorbing light from another primary light source, the vaporized sample may become excited to fluoresce, and the fluorescent emission may be analyzed spectroscopically for purposes of chemical analysis of the sample. It is to be understood that only because of the highly controlled and stable vaporization of the sample from the anode, due to the action of the metastable argon stream playing over the anode, that these methods of spectroscopic analysis are possible in a straight-forward, reproducible, and accurate manner.

The characteristic emission of light by the sample material takes place primarily in the portion of the arc 12 in the space between the anode 16 and the nozzle 26. The characteristic light emission is most intense in the region close to the anode 16, as indicated by the arrows 100 radiating from this region of the arc 12 in FIG. 1. Any suitable type of spectroscopic equipment may be employed for spectroscopically analyzing the light emitted from the arc 12.

The cathode ballast chamber 50 may vary in size and shape. The relief aperture or leak 56 leading out of the cathode ballast chamber 50 may also vary in size.

The striker rod 90 may be of a small diameter so that it will be vaporized rapidly by the arc current. For example, the graphite striker rod 90 may have a diameter of about 0.2–0.3 of a millimeter.

While the use of the slender striker rod 90 to strike the arc is highly advantageous, it is possible in some cases to strike the arc in other ways. For example, the orifice 38 in the gas shaping nozzle 36 may be made large enough so that the anode electrode 16 can be inserted through the orifice 38 and inside the arc chamber 34 until the anode electrode either physically touches the cathode electrode ring 14 or is so close to the cathode that an electrical spark can be employed to bridge the distance between the anode and the cathode to establish an electrically conductive path for the arc to follow therebetween.

Another way to strike the arc is to position the anode 16 just outside the orifice 38 in the gas shaping nozzle 36 and to produce a high voltage spark discharge or a radio frequency discharge between the electrodes, in combination with a uniquely shaped gas flow out of the nozzle and against the anode. It is also possible to strike the arc by using a third, intermediate, "tickler" electrode between the anode and the cathode to assist in initiating a high voltage spark discharge or a radio frequency discharge. A high voltage to cause the discharge may be provided beween the tickler electrode and either the cathode or the anode, preferably the cathode.

However, these alternative methods of striking the arc are restrictive, in that these methods may require a unique shape of the arc chamber or the gas shaping nozzle, just to initiate the discharge. A requirement of this kind is not desirable, because it is decidedly preferable to employ such variable features as the shape, volume and size of the arc chamber, the cathode electrode ring and the gas shaping nozzle to provide for control of the shape, direction and laminarity of the metastable argon "beam" emerging from the gas shaping nozzle. Such variable features should preferably be used to establish the manner in which the arc impinges upon the sample-containing anode electrode, so that such factors as the sample evaporation rate can be controlled and varied.

The provision of the slender striker rod, functioning as an extension of the anode electrode, makes it possible to strike the arc by bringing the striker rod into physical contact with the cathode, regardless of the size and shape of the gas shaping nozzle, the arc chamber and the cathode electrode. The striker rod has the advantage of being quickly destroyed by the resistance heating produced by the arc current, once the arc has been established between the rod and the cathode. Even more importantly, the arc is forced to follow the path defined by the vaporized striker rod, out of the arc chamber, through the orifice in the gas shaping nozzle, and to the anode, independently of the flow rate of the metastable argon, and/or the shape of the arc chamber, and/or the shape of the gas shaping nozzle. As a result, these features, as well as the nature of the gas as such, may be selected to optimize the arc behavior at the anode. There is no need to make compromises as to these features to provide for the striking of the arc discharge.

Thus, while it is possible in some fortuitous circumstances to initiate the arc discharge without using the striker rod, it is much more advantageous to employ the striker rod, because the arc can be started much more easily, and because the operation of the arc can be controlled to much better advantage after the arc has been started.

I claim:

1. A stabilized arc device to produce light for spectroscopic analysis, said device comprising a housing having a chamber therein, a cathode within said chamber,
an anode electrode outside said housing,
direct current electrical power supply means having positive and negative terminals connected to said respective anode and cathode electrodes,
gas supply means for introducing a pressurized stabilizing gas into said chamber,
a nozzle electrode having a gas discharge orifice therein and disposed on said housing for discharging a stream of the stabilizing gas from said chamber to said anode electrode to stabilize an electrical arc between said cathode and anode electrodes,
said nozzle electrode being made of an electrically conductive material,
and electrically insulating means for insulating said nozzle electrode from said housing and also from said cathode and anode electrodes whereby said nozzle electrode can assume an intermediate electrical potential between the electrical potentials of said cathode and anode electrodes,
said anode electrode having receptacle means for holding a sample material to be vaporized by the arc to produce light for spectroscopic analysis.

2. A device according to claim 1,
in which said nozzle electrode is left floating electrically without any connection to said electrical power supply means and without any connection to said cathode and anode electrodes other than the conductive path afforded by said electrical arc.

3. A device according to claim 1,
in which said cathode electrode has an opening therein,
said device including means for producing an outward flow of some of the stabilizing gas from said chamber and through said opening in said cathode electrode to cause the arc to maintain a cathode spot within said opening in said cathode electrode.

4. A device according to claim 1,
in which said electrodes and said chamber are disposed substantially along a common axis,
said gas supply means including a plurality of gas inlets extending into said chamber and spaced uniformly around said axis,
said gas inlets being directed at angles having circumferential components about said axis to produce a whirling motion of the gas within said chamber.

5. A device according to claim 1,
in which said gas supply means comprises means for supplying argon as the stabilizing gas.

6. A device according to claim 1,
in which said cathode electrode has an opening therein,
said device including means for producing an outward flow of some of the stabilizing gas from said chamber and through said opening in said cathode electrode to cause the arc to maintain a cathode spot within said opening in said cathode electrode,
said chamber, said anode electrode, said orifice and said opening being disposed substantially along a common axis,
said gas supply means including a plurality of gas inlets extending into said chamber and spaced uniformly around said axis,
said gas inlets being directed at angles having circumferential components about said axis to produce a whirling motion of the gas within said chamber.

7. A stabilized arc device to produce light for spectroscopic analysis,
said device comprising a housing having a chamber therein,
a first electrode within said chamber,
a second electrode outside said housing,
direct current electrical power supply means having oppositely polarized terminals connected to said respective first and second electrodes,
gas supply means for introducing a pressurized stabilizing gas into said chamber,
a nozzle electrode having a gas discharge orifice therein and disposed on said housing for dicharging a stream of the stabilizing gas from said chamber to said second electrode to stabilize an electrical arc between said first and second electrodes,
said nozzle electrode being made of an electrically conductive material,
electrically insulating means for insulating said nozzle electrode from said housing and also from said first and second electrodes whereby said nozzle electrode can assume an intermediate electrical potential between the electrical potentials of said first and second electrodes,
and means for introducing a sample material into the arc for vaporization by the arc to produce light for spectroscopic analysis,
said first electrode having an opening therein connecting with said chamber,
said device including means for producing an outward flow of some of said stabilizing gas through said opening in said first electrode to cause the arc to maintain an electrode spot within said opening in said first electrode.

8. A device according to claim 7,
in which said chamber, said orifice, said opening in said first electrode and said second electrode are disposed substantially along a common axis,
said gas supply means including a plurality of gas inlets extending into said chamber and spaced uniformly around said axis,
said gas inlets being directed at angles having circumferential components about said axis to produce a whirling motion of the gas within said chamber.

9. A stabilized arc device to produce light for spectroscopic analysis,
said device comprising a housing with a chamber therein having a generally circular cross-section,
a cathode electrode disposed generally axially within said chamber,
an anode electrode disposed substantially axially outside said housing,
gas supply means for introducing a pressurized stabilizing gas into said chamber,
orifice means on said housing and forming a generally axial orifice connecting with said chamber for discharging a stream of the stabilizing gas from said chamber to said anode electrode to stabilize an electrical arc between said cathode and anode electrodes for producing light for spectroscopic analysis,
said anode electrode having receptacle means for holding a sample material to be vaporized by said arc for spectroscopic analysis,
said cathode electrode having a generally axial opening therein,
and means for producing an outward flow of some of the stabilizing gas from said chamber and through said opening in said cathode electrode to cause the arc to maintain a cathode spot within said opening in said cathode electrode.

10. A device according to claim 9,
including flow restricting means for restricting the outward flow of the stabilizing gas through said opening in said cathode electrode,
said opening in said cathode being disposed between said chamber and said flow restricting means.

11. A device according to claim 9,
including flow restricting means for restricting the outward flow of the stabilizing gas through said opening in said cathode electrode,
said opening in said cathode electrode being disposed between said chamber and said flow restricting means,
said flow restricting means having a flow restricting orifice therein which is smaller in cross-section than said opening in said cathode electrode.

12. A device according to claim 9,
in which said orifice means comprise a nozzle electrode having said axial orifice therein,
said nozzle electrode being made of an electrically conductive material,
and electrically insulating means for insulating said nozzle electrode from said housing and also from said cathode and anode electrodes whereby said nozzle electrode can assume an intermediate electrical potential between the electrical potentials of said cathode and anode electrodes.

13. A device according to claim 9,
in which said chamber, said anode electrode, said orifice and said opening are disposed substantially along a common axis,
said gas supply means including a plurality of gas inlets extending into said chamber and spaced uniformly around said axis,
said gas inlets being directed at angles having circumferential components about said axis to produce a whirling motion of the gas within said chamber.

14. A stabilized arc device to produce light for spectroscopic analysis,
said device comprising a housing having a chamber therein,
a first electrode within said chamber,
a second electrode outside said housing,
gas supply means for introducing a stabilizing gas into said chamber,
orifice means on said housing forming an orifice connecting with said chamber for discharging a stream of the stabilizing gas from said chamber to said second electrode to stabilize an electrical arc between said first and second electrodes for producing light for spectroscopic analysis,
means for introducing a sample material into the arc for vaporization by the arc,
said first electrode having an opening therein connecting with said chamber,
and means for producing an outward flow of some of said stabilizing gas through said opening in said first electrode to cause the arc to maintain an electrode spot within said opening in said first electrode.

15. A device according to claim 14,
in which said orifice, said opening in said first electrode, and said second electrode are disposed substantially along a common axis.

16. A device according to claim 14,
in which said gas supply means takes the form of means for supplying argon as the stabilizing gas.

17. A device according to claim 14,
including flow restricting means for restricting the outward flow of the stabilizing gas through said opening in said first electrode.

18. A device according to claim 14,
including flow restricting means having a flow restricting orifice for restricting the outward flow of the stabilizing gas through said opening in said first electrode,
said opening being disposed between said chamber and said flow restricting orifice.

19. A device according to claim 14,
in which said orifice means include a conductive nozzle electrode having said orifice therein,
and electrically insulating means for insulating said nozzle electrode from said housing and also from said first and second electrodes whereby said nozzle electrode can assume an intermediate electrical potential between the electrical potentials of said first and second electrodes.

20. A device according to claim 14,
in which said chamber, said orifice and said opening are disposed substantially along a common axis,
said gas supply means including a plurality of gas inlets extending into said chamber and spaced uniformly around said axis,
said gas inlets being directed at angles having circumferential components about said axis to produce a whirling motion of the gas within said chamber.

21. A stabilized arc device to produce light for spectroscopic analysis,
said device comprising a housing with a chamber therein having a generally circular cross-section,
a cathode electrode disposed generally axially within said chamber,
an anode electrode disposed substantially axially outside said housing,
gas supply means for introducing a pressurized stabilizing gas into said chamber,
orifice means on said housing and forming a generally axial orifice connecting with said chamber for discharging a stream of the stabilizing gas from said chamber to said anode electrode to stabilize an electrical arc between said cathode and anode electrodes for producing light for spectroscopic analysis,
means for supplying a sample material to the arc for vaporization by said arc for spectroscopic analysis,
said cathode electrode having a generally axial opening therein,
means for producing an outward flow of some of the stabilizing gas from said chamber and through said opening in said cathode electrode to cause the arc to maintain a cathode spot within said opening in said cathode electrode,
and an electrically conductive generally axial striker rod mounted initially on said anode electrode and extending through said orifice and into said chamber for engagement with said first electrode to strike an electrical arc,
said striker rod having an end portion for insertion into said opening in said cathode electrode,
said end portion having an outwardly projecting electrically conductive thread thereon for engaging said cathode electrode to strike the arc.

22. A device according to claim 21, in which said striker rod and said thread are made of graphite.

23. A device according to claim 21, in which said thread and said striker rod have sufficient electrical resistance to provide for rapid vaporization of said thread and said striker rod to establish the arc between said anode and cathode electrodes.

* * * * *

UNITED STATES PATENT OFFICE
CERTIFICATE OF CORRECTION

Patent No. 4,060,708     Dated Nov. 29, 1977

Inventor(s)   John P. Walters

It is certified that error appears in the above-identified patent and that said Letters Patent are hereby corrected as shown below:

Column 9, line 1, after "cathode" insert --electrode--

Signed and Sealed this

Twenty-eighth Day of March 1978

[SEAL]

Attest:

RUTH C. MASON
*Attesting Officer*

LUTRELLE F. PARKER
*Acting Commissioner of Patents and Trademarks*

UNITED STATES PATENT OFFICE
CERTIFICATE OF CORRECTION

Patent No. 4,060,708  Dated Nov. 29, 1977

Inventor(s) John P. Walters

It is certified that error appears in the above-identified patent and that said Letters Patent are hereby corrected as shown below:

Column 1, at the beginning of the specification, insert

-- The Government has rights in this invention pursuant to Grant No. GP-7795 awarded by the National Science Foundation. --

Signed and Sealed this

Twenty-first Day of November 1978

[SEAL]

Attest:

RUTH C. MASON  
Attesting Officer

DONALD W. BANNER  
Commissioner of Patents and Trademarks